(12) United States Patent
Freeman et al.

(10) Patent No.: US 8,082,808 B2
(45) Date of Patent: Dec. 27, 2011

(54) AIR SAMPLING SYSTEM

(75) Inventors: Linda L. Freeman, Rancho Murieta, CA (US); Heidi C. Hayes, Folsom, CA (US); Bradley A. Mosakowski, Shingle Springs, CA (US); Donald L. Smith, West Newton, PA (US); Mark A. McFeely, Monongahela, PA (US); Saulius Trakumas, Pittsburgh, PA (US); Linda S. Coyne, Pittsburgh, PA (US)

(73) Assignee: Airlab Home Kit, Folsom, CA (US)

( * ) Notice: Subject to any disclaimer, the term of this patent is extended or adjusted under 35 U.S.C. 154(b) by 0 days.

(21) Appl. No.: 12/658,676

(22) Filed: Feb. 12, 2010

(65) Prior Publication Data

US 2011/0197686 A1 Aug. 18, 2011

(51) Int. Cl.
*G01N 1/00* (2006.01)
(52) U.S. Cl. .................................................. 73/863.21
(58) Field of Classification Search .................. None
See application file for complete search history.

(56) References Cited

U.S. PATENT DOCUMENTS

| | | | | | |
|---|---|---|---|---|---|
| 3,884,081 | A | * | 5/1975 | Griffith | 73/863.31 |
| 4,119,403 | A | * | 10/1978 | Rex | 436/122 |
| 4,140,011 | A | * | 2/1979 | Krupa et al. | 73/170.17 |
| 5,847,291 | A | * | 12/1998 | Green et al. | 73/863.33 |
| 5,898,114 | A | * | 4/1999 | Basch et al. | 73/863.23 |
| 6,607,700 | B1 | * | 8/2003 | Apte et al. | 422/91 |
| 2005/0279182 | A1 | * | 12/2005 | Cole et al. | 73/864.71 |
| 2008/0229805 | A1 | * | 9/2008 | Barket et al. | 73/31.01 |
| 2010/0050750 | A1 | * | 3/2010 | Saaski et al. | 73/61.75 |
| 2010/0104473 | A1 | * | 4/2010 | Kirollos et al. | 422/58 |

OTHER PUBLICATIONS

SKC, Inc.; Comprehensive Catalog & Air Sampling Guide; UME-100 Passive Sampler for Formaldehyde; 2001; p. 65.

* cited by examiner

*Primary Examiner* — Robert Raevis
(74) *Attorney, Agent, or Firm* — Heisler & Associates (57) ABSTRACT

The system includes at least one sampler including a body having a hollow interior accessed through holes in the body and optionally a slide which can selectively cover and expose the holes in the body. A stand is provided made of a base and a floor. The base includes at least one recess therein. The recess is configured to support the sampler therein so that the sampler can be held by the stand while sampling an airspace at a particular location. The floor can be separated at least partially from the base in a removably attachable fashion to provide selective access to a hollow inside. A sampler can be placed within this hollow inside space and resealed so that the stand doubles as a shipping container for the sampler after collection of an air sample.

10 Claims, 5 Drawing Sheets

AIR SAMPLING SYSTEM

FIELD OF THE INVENTION

The following invention relates to samplers and other systems for measuring air quality and the presence of various different gases or other target constituents within the air of a space to be monitored. More particularly, this invention relates to air sampling systems which include both a stand for holding an air sampler and packaging for allowing the return of an air sample in a sealed and secure fashion, and associated methods.

BACKGROUND OF THE INVENTION

Systems for sampling the air come in a variety of different configurations. Some air samplers collect an air sample for later analysis while other sensors provide both collection and testing of an air sample to determine the prevalence of target constituents. Still other air samplers particularly focus on the detection of a particular chemical or class of chemicals, either providing real time feedback as to the prevalence of target constituents in the air, or requiring laboratory testing to evaluate the prevalence of the target constituent.

While some chemical constituents in the air can be relatively easily identified through appropriate detector technology, other target constituents are less readily detectable, either because of the nature of the target constituent's chemistry or because the target constituent is present in exceptionally low quantities. When the target constituents can be readily detected, devices such as smoke alarms and carbon monoxide alarms are facilitated which can both sample for the target constituent, and when such a target constituent is detected, activate an alarm. When the target constituent requires more elaborate testing to accurately evaluate the prevalence of the target constituent, the sampler must capture a representative sample of air and then seal that sample effectively until it can be analyzed at an appropriate laboratory using testing criteria adapted for the detection of the constituents of interest.

Such air collection type samplers can in a simplest form merely be an enclosure which can be opened, purged, allow an air sample to pass therein and then closed to capture the sample therein. While such simple samplers are generally effective in capturing a sample of air, they are less effective when capturing target constituents that are present in very low quantities, or which might be present only during certain parts of the day and not always present.

Materials are known which selectively adsorb some chemical constituents more than others. When a particular target constituent is to be sampled, a material which preferentially adsorbs that material can be provided within a sealed sampler enclosure. A sampler enclosure can be opened and remain open for a set period of time. The material within such a sampler will selectively adsorb the target constituent in an amount corresponding with the prevalence of that constituent within the air. After the sampling interval is complete the sampler is sealed closed and the preferentially adsorbent material is analyzed in a laboratory. Through appropriate analysis and associated calibration; measurements, such as "parts per million" of the constituent to be measured, can be determined.

Such samplers which expose a material which preferentially adsorbs certain target constituents over a period of time, and then are returned to a laboratory for analysis are most preferable for the measurement of certain constituents and are the type of sampler to which this invention is primarily directed. Such samplers in one form are worn as a badge. The wearer attaches the badge to the wearer's clothing or otherwise wears the badge, such as suspended from a lanyard about the wearer's neck, and the badge travels with the wearer throughout the wearer's day. The sampler within the badge is continuously adsorbing the chemical for which the adsorbent material is preferentially configured. After a period of time has elapsed, such as one day or one week or one month, the sampler is returned to a laboratory and analyzed to determine how much of the constituent being sent has been gathered. This data can then be correlated to an overall amount of exposure that the wearer had to the particular chemical involved.

In one form, such badges include a sampler having an elongate rectangular body with a slide that slides from a lower end of the body to an upper end of the body. Holes are provided in an upper end of the body which pass into an interior of the body. A selectively adsorbent material or merely a material of generally adsorbent nature is contained within the interior. When the slide is in the lower position and the holes are exposed, air surrounding the body passes through the holes and constituents within the air are adsorbed. When the sampling interval is over, the slide can be slid to the upper end to cover the openings and preclude the adsorbent material within the interior from continuing to sense. In this way, the sampler is not contaminated by coming into contact with target constituents after the sampler has left the proximity of the wearer of the badge and before the collected sample is examined in the laboratory. One supplier of such air sampling badges is SKC Inc. of Eighty-Four, Pa.

One problem with such samplers is that when configured in the form of a badge, they cannot effectively monitor the air within a single location, but rather monitor exposure of the wearer to different chemicals. On occasion it is desirable to measure the prevalence of certain target constituents within a particular space, rather than having the sampler follow an individual. For instance, when purchasing a home it would be desirable to have an objective measurement of the prevalence of certain constituent chemicals or classes of chemicals within the home.

Accordingly, a need exists for a sampler which can effectively monitor the prevalence of certain target constituents within a particular space. Furthermore, it is desirable that such samplers be easily returned to a laboratory in a sealed fashion so that the sampler does not become exposed to target constituents when in transit back to the laboratory, and after the sampling interval is complete.

SUMMARY OF THE INVENTION

With this invention, an air sampling system is provided including at least one sampler and at least one stand for the sampler. The stand supports the sampler when it is in use sensing air within a particular location. The stand also has a hollow inside space which doubles as a container for the sampler after the sampler has completed its sampling interval. The sampler can be placed within an interior of the stand and the stand encloses the sampler to keep the sampler from coming into contact with target constituents while the sampler and associated stand/package are in transit back to a laboratory for analysis.

The sampler is generally similar to badge type samplers described above, and including an elongate body extending from a lower end to an upper end with holes adjacent the upper end extending into an interior where an adsorbent material is contained suitable for the target constituent to be measured. A slide slides along the front side of the body from the lower end to the upper end. When the slide is adjacent the lower end, the holes are revealed for sampling. When the slide is adjacent the upper end, the holes are covered and precluded from allowing constituents of the air surrounding the sampler to pass through the openings and adjacent the adsorbent material within the interior of the sampler.

The stand generally includes a base and a floor. The base is configured to rest upon an underlying surface and includes at least one recess in a top panel thereof. This recess is configured to receive the at least one sampler within the recess with an upper end of the sampler including the holes therein above the recess and open for receipt of chemical constituents of the air. The floor of the stand is at least partially removably attachable from the base in a manner which substantially seals an inside space of the stand from coming into contact with surrounding air.

Furthermore, the floor includes a well therein into which a separate sample containment case can rest, and with lower portions of the at least one recess in the base pressing against the case to keep the case within the well. In this way, the case is prevented from being jostled about within the interior of the base, keeps contents within the base organized and provides a secure package for return to a laboratory for further analysis.

OBJECTS OF THE INVENTION

Accordingly, a primary object of the present invention is to provide an air sampling system which allows for the sampling of an air space within a single location in a convenient and reliable fashion.

Another object of the present invention is to provide a stand for an air sampler which can both hold the air sampler while the air sampler is sampling air within a location, and also have a hollow inside which can contain the sampler, such as for shipping back to a laboratory for analysis.

Another object of the present invention is to provide an air sampling method which simplifies the process of sampling air within a space.

Another object of the present invention is to provide an air sampling method which reliably measures constituents of air within a particular space.

Another object of the present invention is to provide a stand for an air sampler which doubles as a sealed shipping container for a sampler.

Other further objects of the present invention will become apparent from a careful reading of the included drawing figures, the claims and detailed description of the invention.

DESCRIPTION OF THE PREFERRED EMBODIMENT

Referring to the drawings, wherein like reference numerals represent like parts throughout the various drawing figures, reference numeral 10 (FIG. 1) is directed to a system for air sampling including samplers 12, 14, 20 (FIGS. 1 and 10-18) as well as a stand for containment of the sampler 20 in a sealed manner for return, such as back to a laboratory. The stand includes a base 50 which can be coupled to a floor 80 to form the complete enclosure of the stand according to this invention (FIGS. 2-9).

Figure 1:
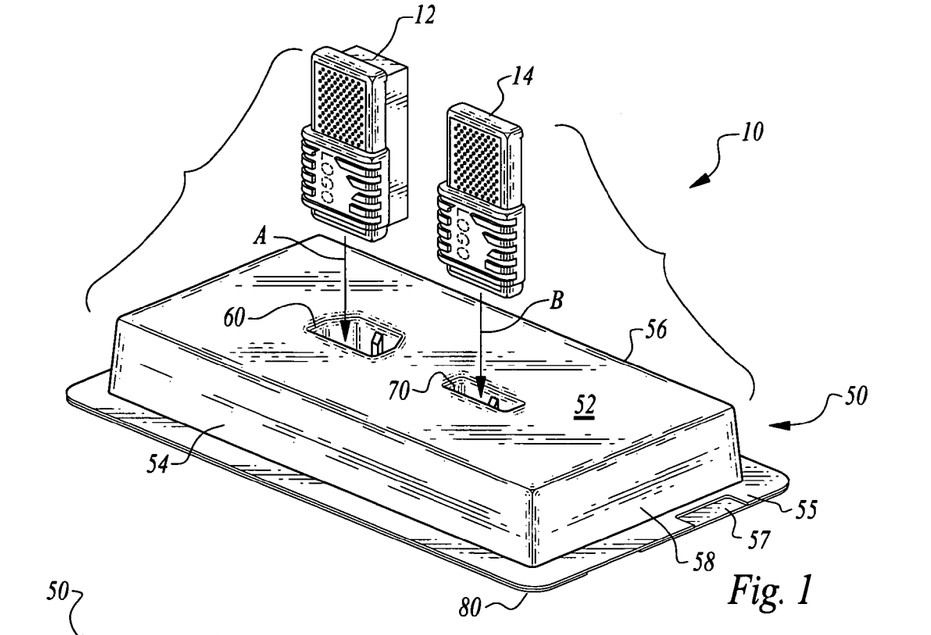
FIG. 1 is a perspective view of the system of this invention including two different types of samplers adjacent a pair of recesses within a top panel of a base of the stand, for support of the samplers in a location in which the air is to be sampled.
Figure 2:
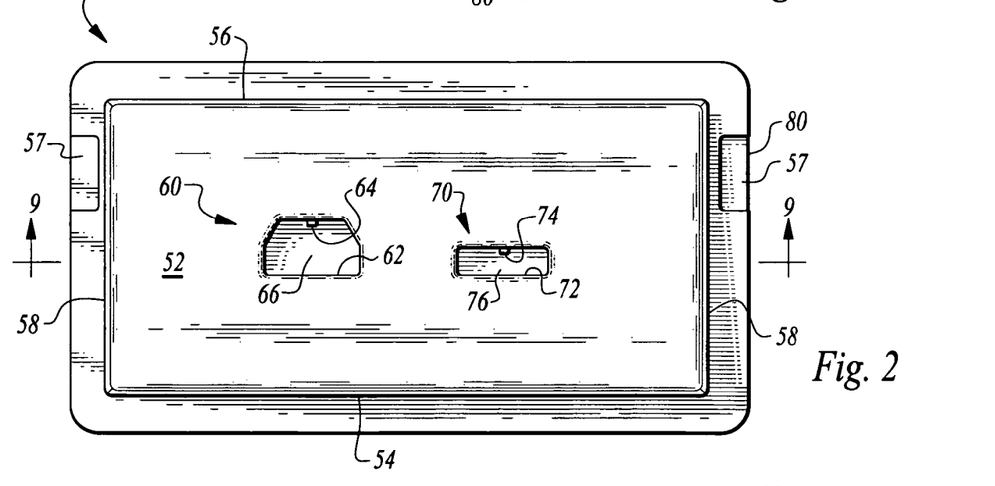
FIG. 2 is a top plan view of the stand portion of that which is shown in FIG. 1.
Figure 3:
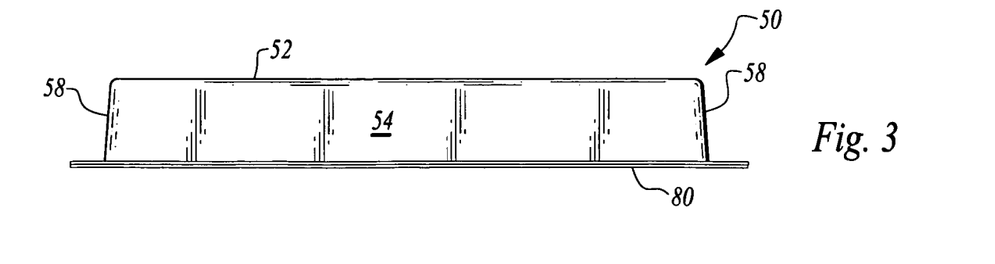
FIG. 3 is a front elevation view of that which is shown in FIG. 2.
Figure 4:
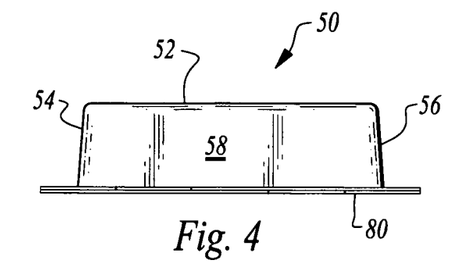
FIGS. 4 and 5 are left and right end views of that which is shown in FIG. 2.
Figure 5:
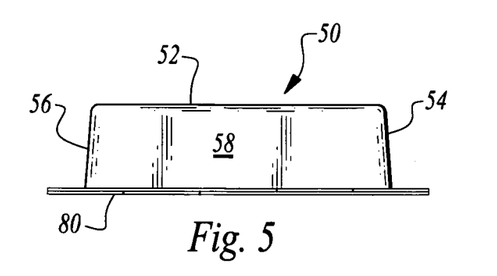
Figure 6:
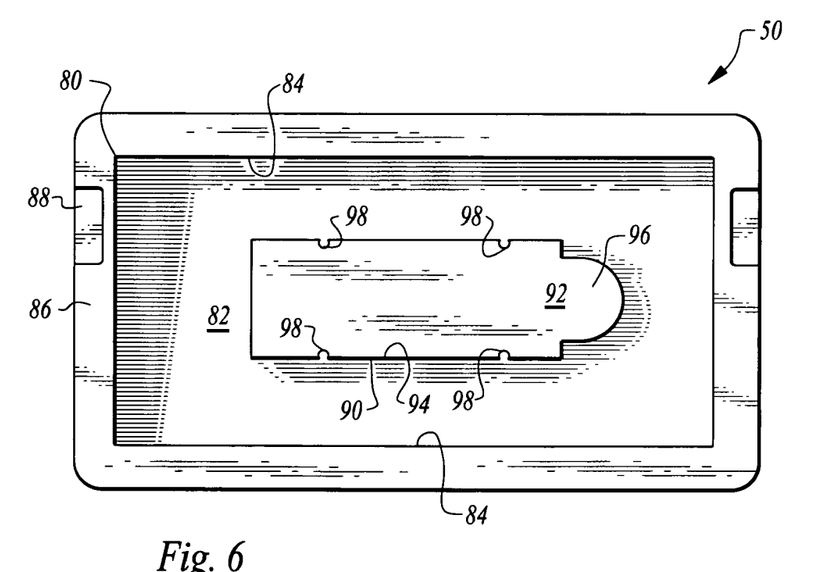
FIG. 6 is a bottom plan view of that which is shown in FIG. 2.
Figure 7:
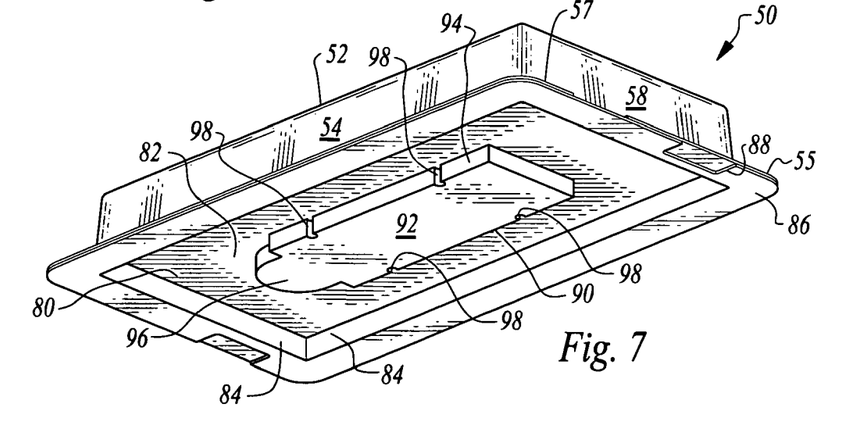
FIG. 7 is a perspective view from below of that which is shown in FIG. 2.
Figure 8:
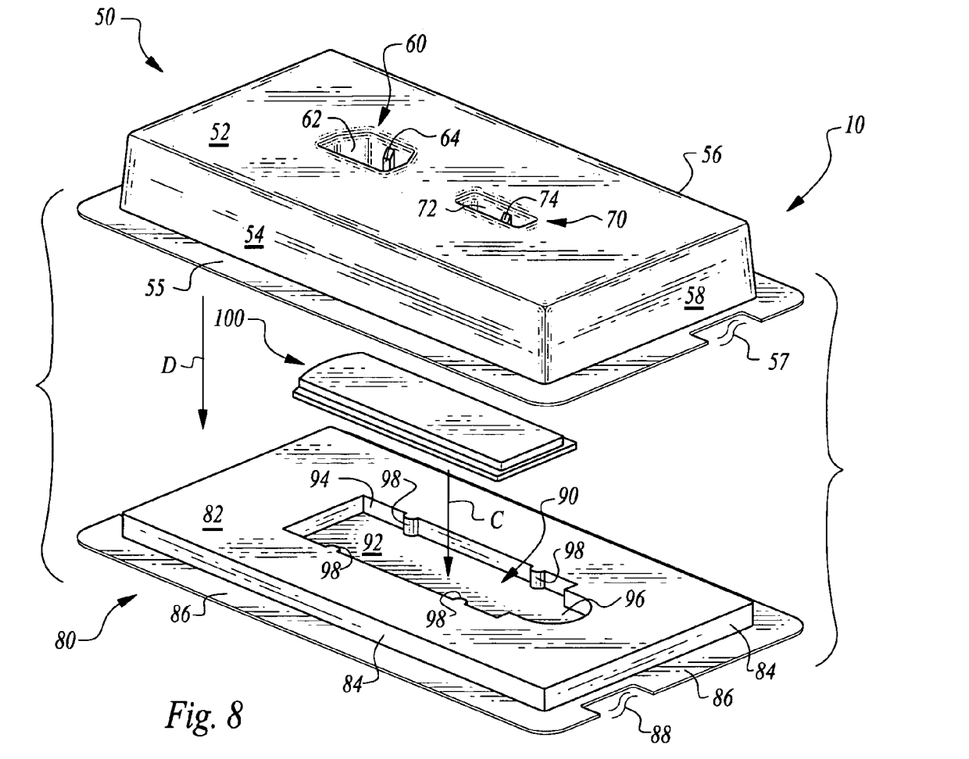
FIG. 8 is an exploded parts view of that which is shown in FIG. 2 and with a sample containing case in the process of being inserted into a well in a floor of the in the form of a shipping container for sealed transport back to a laboratory.
Figure 9:
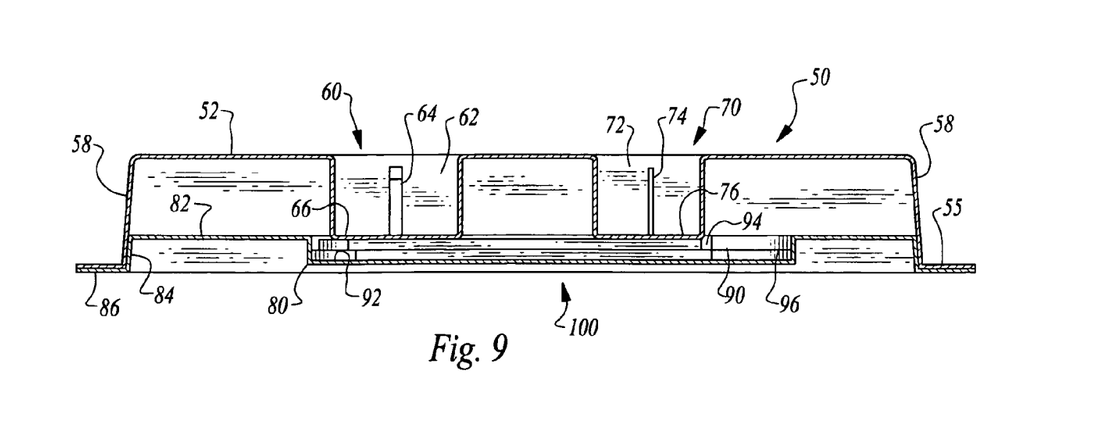
FIG. 9 is a full sectional view of that which is shown in FIG. 2, and revealing how the case can be held tightly within the well within the floor of the stand during shipping return to a laboratory or other analysis location.
Figure 10:
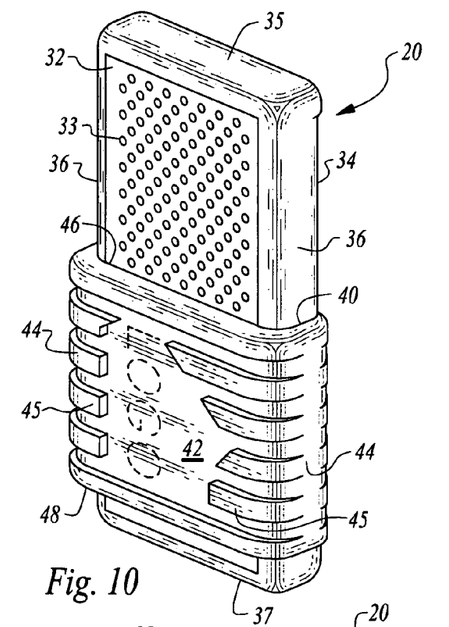
FIG. 10 is a perspective view of a representative sampler for use according to the air sampling system of this invention.
Figures 11, 12:
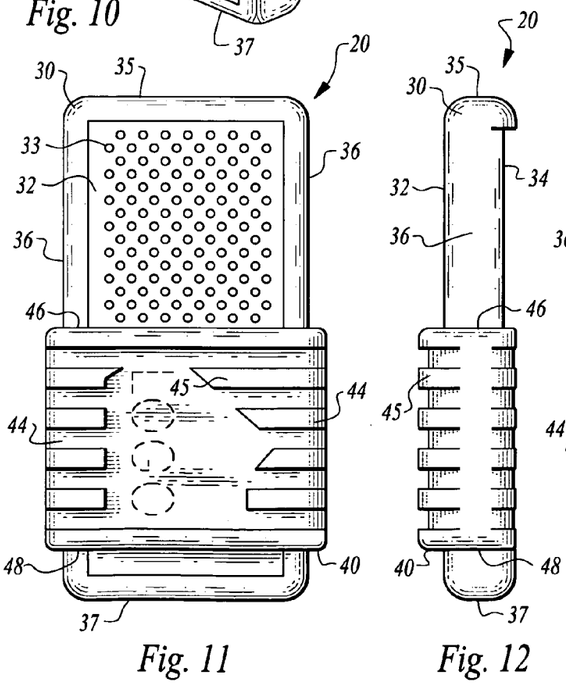
FIG. 11 is a front elevation view of that which is shown in FIG. 10, with the slide in a lower position exposing the openings.
FIG. 12 is a side elevation view of that which is shown in FIG. 10.
Figure 13:
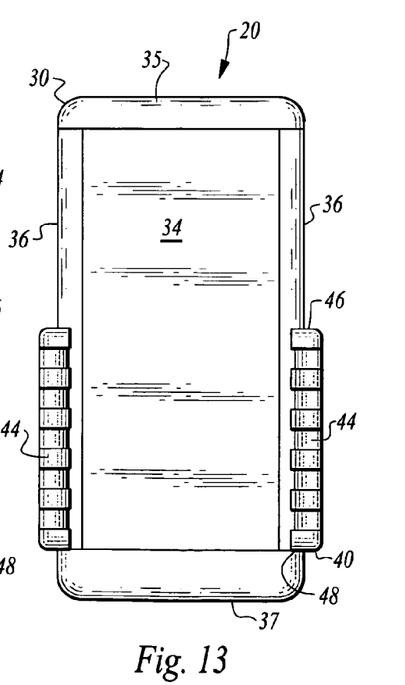
FIG. 13 is a rear elevation view of that which is shown in FIG. 10.
Figure 14:
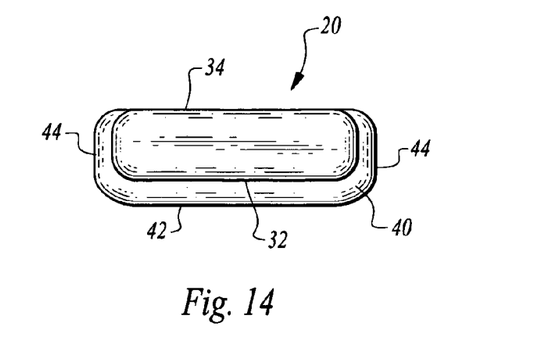
FIG. 14 is a top plan view of that which is shown in FIG. 10.
Figure 15:
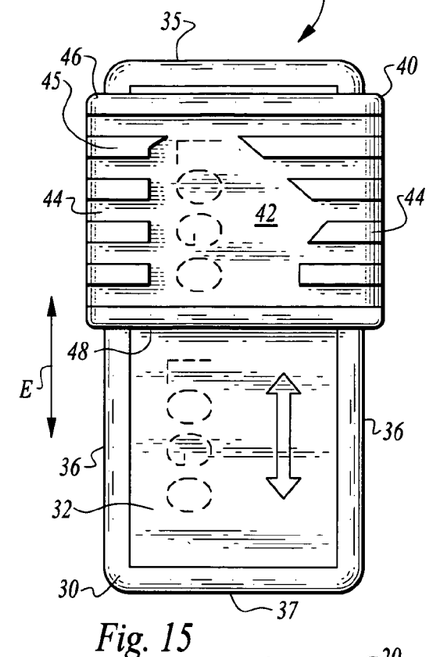
FIG. 15 is a front elevation view of that which is shown in FIG. 10, but with the slide slid to an upper end of the body of the sampler to cover holes extending into an interior of the body of the sampler.

In essence, and with particular reference to FIGS. 1, 8 and 9, basic details of the air sampling system of this invention are described, according to a preferred embodiment. The system 10 includes at least one sampler 20 (FIGS. 10-18) and the stand in the form of a combination of the base 50 and the floor 80. The sampler 20 includes a body 30 of generally rectangular elongate form with a substantially constant thickness and a hollow interior which can contain an adsorbent material for selectively adsorbing a target constituent or generally adsorbing all constituents of the air over time. A slide 40 preferably slides along the body 30 to selectively allow or preclude access of air into the interior of the body 30.

The base 50 of the stand is generally rectangular in form with a top panel 52 which includes at least one recess 60, 70 therein, and in this embodiment both a thick recess 60 and a thin recess 70. The thick recess 60 can support a thick sampler 12, 20 (FIGS. 1 and 16-18) and the thin recess 70 can receive a thin sampler 14, 20 (FIGS. 1 and 10-15). The floor 80 has a perimeter which mates with a perimeter of the base 50 to provide a sealing enclosure which can contain one of the samplers 12, 14, 20 therein. A well 90 in the floor 80 preferably is particularly contoured to receive a sample containment case 100 held tight within the well 90, both by a contour of the well 90 and also lower portions of at least one of the recesses 60, 70 extending down from the top panel 52 of the base 50. The case 100 is thus held securely within a substantially airtight compartment along with the sampler 20 during transport back to an analysis laboratory or other analysis location.

More specifically, and with particular reference to FIGS. 1 and 10-18, particular details of the sampler 20 of this invention are described, according to this preferred embodiment. While the sampler 20 could have a variety of different configurations, in this embodiment, the sampler 20 is generally in the form of a hollow elongate rectangular body 30 which contains an adsorbent material therein. The adsorbent material within the interior can be any suitable material known in the prior art for air sampling which can either be particularly configured to selectively adsorb a target constituent or can merely generally adsorb elements and components it encounters, to provide a representative average sampling of constituents within the air over the sampling interval.

The body 30 generally includes a planar front side 32 opposite a planar rear side 34. Perimeter sides 36 join the front side 32 and rear side 34 together. The rear side 34 can optionally include an expansion area 38 which increases a thickness of the body 30 to form the thick sampler 12 (FIG. 1). Without such an expansion area 38, the sampler 20 is in the form of the thin sampler 14 (FIG. 1). In the embodiment of FIG. 1, both types of samplers 12, 14 are provided which are designed to collect distinct air constituents that require the expansion area 38 or not for the particular type of sampler 12, 14 and associated constituent being sampled.

The front side 32 includes holes 33 adjacent an upper end 35 and with a lower end 37 opposite the upper end 35 which does not include holes 33 adjacent thereto. The holes 33 pass entirely into an interior of the body 30 to allow constituents of the air to pass into and out of the interior of the body 30 of the sampler 20.

The sampler 20 also preferably includes a slide 40 which acts as a cover to selectively cover and expose the holes 33. This slide 40 is located adjacent the front side 32 of the body 30 and includes a main wall 42 having a size similar to a space on the front side 32 that includes the holes 33 thereon. Side curving walls 44 are adjacent each lateral edge of the main wall 42 and wrap around the perimeter sides 36 of the body 30. The main wall 42 has a height extending between a top edge 46 and a bottom edge 48 which is similar to a height of a space on the front side 32 including the holes 33 thereon. The slide 40 can thus completely cover the holes 33 when the slide 40 is adjacent the upper end 35 of the body 30.

An outer surface of the slide 40 preferably includes relief bands 45 thereon. These relief bands increase an amount of friction experienced when a user pushes laterally on the slide 40 to make the slide 40 more easily move between the upper end 35 and lower end 37 of the body 30. The slide 40 preferably sizes the side curving walls 44 to tightly hold the slide 40 adjacent the body 30, and to require significant force to move the slide 40. In this way, the slide 40 is less prone to inadvertent movement, such as by gravity or being jostled, or being inadvertently handled by passersby not understanding the importance of keeping the slide 40 in the desired position.

Typically, the sampler 20 would initially be supplied to a user within a sealed package. The sampler could also as a redundant matter include the slide 40 adjacent the upper end 35. The user would open the sealed packaging and move the slide 40 from the upper position to the lower position (along arrow E of FIG. 15). The holes 33 are then exposed and the sampler 20 commences sampling of the surrounding airspace. The sampler 20 can then be placed within one of the recesses 60, 70 in the base 50 of the stand (FIG. 1, along arrow A or arrow B). The recesses 60, 70 are sized so that the slide 40 can fit within the recesses 60, 70 along with the sampler 20 so that the recesses 60, 70 help to hold the slide 40 adjacent the lower end 37 of the body 30 of the sampler 20 when the sampler 20 is within one of the recesses 60, 70 of the base 50.

The sampler 20 is thus in a configuration sampling a surrounding airspace when resting within the recesses 60, 70 of the base 50.

The stand including the base 50 is positioned in a representative location within the space to be sampled and is then left alone for the sampling period. This sampling period could be one hour, one day, one week, one month, or other sampling intervals depending on the adsorbent material utilized and the protocol associated with analysis of the sampler, so that results can be appropriately calibrated into meaningful data relating to the prevalence of target constituents within the sampling location's airspace.

With particular reference to FIGS. 1-9, details of the stand including the base 50 and floor 80 are described, according to this preferred embodiment. In this embodiment, the stand includes both the base 50 and the floor 80. It is conceivable that the stand could be formed of a single piece with two separate parts which are attached together, such as by a hinge, rather than two completely separate parts as is the case with the base 50 and the floor 80 of this embodiment.

The base 50 forms a majority of the stand and supports the thick recess 60 and thin recess 70 in the top panel 52 of the base 50, in this preferred embodiment. The base 50 includes a front wall 54, rear wall 56 and side walls 58 which each extend down from edges of the top panel 52 down to a flange 55. This flange 55 is generally parallel with the top panel 52 and extends laterally to define a foot which rests upon a horizontal underlying surface so that the top panel 52 is elevated slightly above this surrounding surface.

A notch 57 is formed in at least one portion of the flange 55 to more easily allow for separation of the base 50 from the floor 80. The walls 54, 56, 58 are preferably each planar and substantially perpendicular to the top panel 52. If desired, representative logos or instructions can be provided on the top panel 52 or walls 54, 56, 58 for effective communication to those viewing the base 50.

As can be seen in FIG. 9, the base 50 is preferably hollow inside and formed from a layer of substantially constant thickness which bends to provide the contour shown. Such a contour for the base 50 can be formed by injection molding or vacuum forming of appropriate plastic materials, as well as other forming techniques. This base 50 is preferably continuous so that air cannot leak through the base 50, so that the stand including the base 50 and floor 80 can be substantially sealed together to isolate the space within the base 50 from a surrounding atmosphere.

Figure 16:
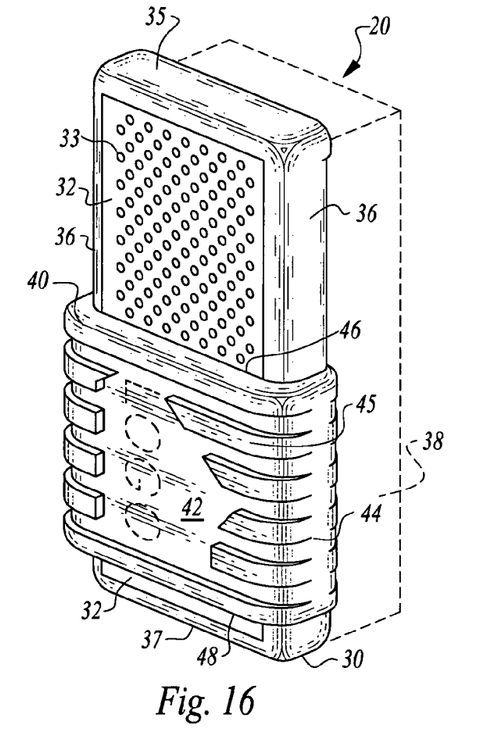
FIG. 16 is a perspective view of an alternative embodiment sampler having a thicker contour.
Figure 17:
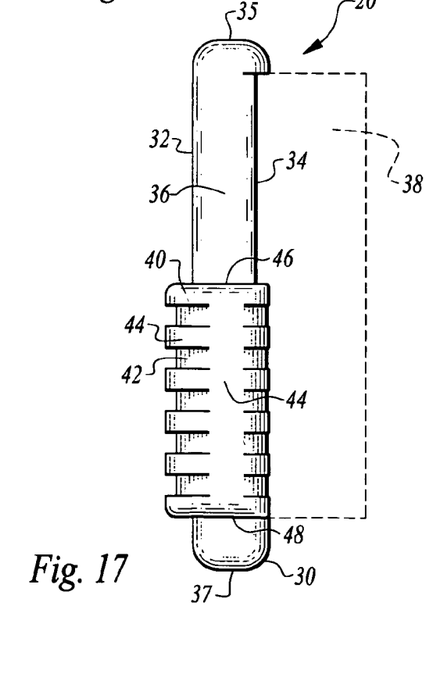
FIG. 17 is a side elevation view of that which is shown in FIG. 16.
Figure 18:
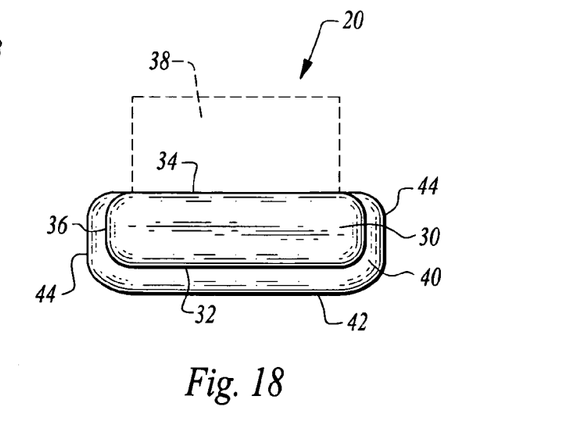
FIG. 18 is a top plan view of that which is shown in FIG. 16.

The base 50 includes a thick recess 60 and thin recess 70 which are similar to each other and extend down from the top panel 52 of the base 50. The thick recess 60 includes perimeter walls 62 which extend vertically down from the top panel 52 and have a contour generally matching a horizontal cross section of the sampler 20 including the extension area 38 (FIGS. 16-18). This thick sampler 12 is also shown in FIG. 1. These perimeter walls 62 are preferably sized to be approximately the same as the lower end 37 of the body 30 of the sampler 20 to be received within the thick recess 60.

A friction tab 64 extends from one of the perimeter walls 62 of the thick recess 60. This friction tab 64 extends sufficiently far into the thick recess 60 so that a friction fit is provided for the sampler 20 when pressed down into the thick recess 60. The friction tab 64 thus helps to hold the thick sampler 12 within the thick recess 60 (FIG. 1).

Similarly, the thin recess 70 includes perimeter walls 72 extending vertically down from the top panel 52. These perimeter walls 72 have a size and shape which matches a contour of the sampler 20 without the extension 38 (FIGS. 10-15) and as represented by the thin sampler 14 of FIG. 1.

The thin recess 70 includes a friction tab 74 in one of the perimeter walls 72 which causes the thin sampler 12 to experience a friction fit when pressed into the thin recess 70.

The thick recess 60 and thin recess 70 include bottom walls 66, 76 generally parallel with a top panel 52 and defining lowermost portions of the recesses 60, 70. As can be seen in FIG. 9, these bottom walls 66, 76 preferably aid in holding one of the samplers 20 securely within the well 90 formed in the floor 80, as described in detail below.

The floor 80 provides a second portion of the stand, along with the base 50, in this preferred embodiment. The floor 80 includes a plateau 82 having a size similar to that of the top panel 52. Raised walls 84 raise the plateau 52 up above a flange 86. The flange 86 preferably has a shape and size complemental with the flange 55 of the base 50 so that the flange 86 of the floor 80 can nest adjacent the flange 55 of the base 50 with the plateau 82 inboard of the walls 54, 56, 58 of the base 50. The raised walls 84 are preferably shorter than the walls 54, 56, 58 so that an open inside space remains between the plateau 82 of the floor 80 and the top panel 52 of the base 50. A notch 88 is formed in the flange 86 of the floor 80 to assist in separating the flange 86 of the floor 80 from the flange 55 of the base 50. The flanges 86, 55 can be sealed together to further preclude migration of air into and out of the interior of the stand.

A well 90 is preferably formed within the plateau 82. This well 90 includes a lower wall 92 having a shape defined by a side contour 94 surrounding this lower wall 92 and extending up to the plateau 82. This side contour 94 is generally similar in shape to that of a separate sample containing case 100 so that the case 100 can reside within the well 90. A depth of the well 90 is preferably similar to but slightly less than a thickness of the case. The lower wall 92 is preferably longer than the case is tall so that a finger space 96 can be provided at one end thereof to facilitate a user placing one's finger into the finger space 96 and then beneath the case 100 to lift the case 100 out of the well 90.

The case 100 can hold an additional form of sampling device other than the samplers 12, 14 (FIG. 1). For instance, a mold testing strip can gather a sample and then be placed in the case 100 for return to the laboratory. The samplers 12, 14 can be used to test for other target constituents and also be returned inside the stand, typically first sealed within individual airtight pouches.

Ribs 98 preferably extend in from the side contour 94 of the well 90 to provide a friction fit for the case 100 pressed into the well 90. The bottom walls 66, 76 of the recesses 60, 70 are directly above this well 90 and spaced only slightly from the lower wall 92, by a distance similar to a thickness of the case 100. In this way, when the floor 80 and base 50 are placed together (by movement of the base 50 along arrow D of FIG. 8) and the case 100 has been placed within the well 90 (by movement of the case 100 along arrow C of FIG. 8) the case 100 is held by the bottom walls 66, 76 of the recesses 60, 70 within the well 90.

In such a configuration, a sampler 20 can have its slide 40 moved to the closed position adjacent the upper end 35 and the sampler 20 can be placed within an interior of the stand to provide a redundant system for ensuring that the interior of the sampler 20 does not come into contact with target chemicals during transport back to a laboratory for analysis. Furthermore, should a user fail to move the slide 40 back to the closed position overlying the holes 33, because the sampler 20 has been contained within the stand, if the laboratory can determine that the stand has not had its integrity violated during shipping, an air sample within the sampler 20 might still be substantially accurate. Furthermore, with such a redundant system, should the stand be damaged in transit and the sealed nature of the stand be compromised, by having the slide 40 in the closed position overlying the holes 33, the sampler 20 will still contain a substantially valid sample therein for testing by a laboratory or other testing facility.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. An air sampling system comprising in combination:
   at least one air sampler;
   said air sampler including an enclosure having sides surrounding an interior with at least one opening through at least one of said sides of said enclosure and accessing said interior;
   a stand adapted to hold said at least one air sampler;
   said stand including at least one recess, said recess sized and shaped to receive a portion of said at least one air sampler therein to hold said air sampler, said recess sized small enough to leave said at least one opening in said air sampler unobstructed;
   wherein said sampler is elongate in form between an upper end and a lower end, said at least one recess adapted to hold said lower end of said sampler with said at least one opening in said sampler located spaced from said lower end and outside of said recess when said lower end of said air sampler is located within said recess;
   wherein said sampler includes a cover adapted to selectively block said opening; and
   wherein said cover includes a slide adapted to slide along said enclosure of said air sampler between said upper end and said lower end, said at least one recess sized large enough to hold said lower end of said air sampler therein with said slide adjacent said lower end.

2. An air sampling system comprising in combination:
   at least one air sampler;
   said air sampler including an enclosure having sides surrounding an interior with at least one opening through at least one of said sides of said enclosure and accessing said interior;
   a stand adapted to hold said at least one air sampler;
   said stand including at least one recess, said recess sized and shaped to receive a portion of said at least one air sampler therein to hold said air sampler, said recess sized small enough to leave said at least one opening in said air sampler unobstructed;
   wherein said at least one recess is sized for a friction fit to hold said air sampler in said recess with frictional engagement between said enclosure of said air sampler and perimeter walls of said recess; and
   wherein said perimeter wall of said at least one recess includes a friction tab reducing a thickness of said recess to cause a thickness of said enclosure of said air sampler to be greater than a thickness of said recess, at least a small amount, to create a friction fit between said enclosure of said air sampler and said recess.

3. The system of claim 2 wherein said stand includes a pair of recesses and wherein a pair of air samplers are provided with one of said air samplers being a thick sampler that is thicker than the other thin sampler, said pair of recesses in said stand including a thick recess and a thin recess with said thick recess having dimensions adapted to cause a friction fit with said thick air sampler and said thin recess having dimensions adapted to cause a friction fit with said thin air sampler.

4. An air sampling system comprising in combination:
   at least one air sampler;
   said air sampler including an enclosure having sides surrounding an interior with at least one opening through at least one of said sides of said enclosure and accessing said interior;
   a stand adapted to hold said at least one air sampler;
   said stand including at least one recess, said recess sized and shaped to receive a portion of said at least one air sampler therein to hold said air sampler, said recess sized small enough to leave said at least one opening in said air sampler unobstructed; and
   wherein said stand includes a hollow inside space, said stand formed of a base portion and a floor portion with said base portion and said floor portion at least partially separable from each other, said base having said at least one recess therein, said hollow inside space of said stand large enough to hold at least one air sampler therein, such that said stand can act as a container for said air sampler.

5. The system of claim 4 wherein said base and said floor of said stand each include a perimeter of similar size and complemental form to allow said floor and said base to seal together when located adjacent each other and to substantially preclude air migration into and out of said hollow inside of said stand.

6. The system of claim 4 wherein said floor portion of said stand includes a well therein, said well having a contour similar to a contour of a sample containing case separate from said sampler, such that said case can fit within said well, said well including a lower wall spaced from a bottom wall of said at least one recess by a distance similar to a thickness of case, such that when said case is placed within said well and adjacent said lower wall of said well, said bottom wall of said recess abuts said case to hold said case within said well and discourage movement of said case within said hollow interior of said stand; and
   wherein said contour of said well includes ribs therein, said ribs spaced from each other by a distance sufficiently small so that said case has a friction fit against said ribs when said case is placed within said well.

7. The system of claim 6 wherein said floor portion of said stand and said base portion of said stand each include a flange extending laterally from perimeters thereof, said flanges adapted to be located adjacent each other when said floor is coupled to said base, said flanges oriented within a common plane, said flanges adapted to support said stand upon an underlying surface.

8. A method for sampling air in a space, including the steps of:
   providing at least one air sampler, said air sampler including an enclosure having sides surrounding an interior with at least one opening through at least one of the sides of the enclosure and accessing the interior of the enclosure;
   providing a stand adapted to hold the at least one air sampler, the stand including at least one recess, the recess sized and shaped to receive a portion of the at least one air sampler therein to hold the air sampler, the recess in the stand sized small enough to leave the at least one opening in the air sampler unobstructed when the air sampler is located within the recess;
   placing the stand on a surface in a location where air is to be sampled;
   inserting the air sampler into the recess with the at least one opening in the air sampler unobstructed by the recess;
   allowing the air sampler to collect an air sample;
   configuring the stand to be hollow inside and openable in a sealing fashion; and
   inserting the air sampler into the inside of the stand and sealed within the interior of the stand after said allowing the air sampler to collect an air sample step.

9. The method of claim 8 including the further step of returning the air sampler to a lab for analysis with the air sampler sealed within the inside of the stand.

10. The method of claim 9 including the further step of configuring the stand to include a base portion and a floor portion with the floor portion and the base portion adapted to substantially seal together when coupled to each other and to be removable at least partially from each other, the floor including a well therein sized to receive a sample containing case separate from the air sampler, and recesses located within the base, the recesses having a depth toward the floor sufficient that a bottom wall of the recess abuts the case when the case is located within the well and the floor portion of the stand is coupled to the base portion of the stand.

* * * * *